(12) United States Patent
Liu et al.

(10) Patent No.: US 6,472,002 B2
(45) Date of Patent: Oct. 29, 2002

(54) DIET FOOD FORMULA FOR OVERWEIGHT PEOPLE AND DIABETICS

(75) Inventors: Xue Wu Liu; Tian Xiao Liu; Xuewen Liu; Rui Li, all of Arcadia, CA (US)

(73) Assignee: Joe Nieh, City of Industry, CA (US)

( * ) Notice: Subject to any disclaimer, the term of this patent is extended or adjusted under 35 U.S.C. 154(b) by 0 days.

(21) Appl. No.: 09/730,415

(22) Filed: Dec. 4, 2000

(65) Prior Publication Data

US 2002/0068110 A1 Jun. 6, 2002

(51) Int. Cl.⁷ .......................... A23L 1/302; A23L 1/304; A23L 1/0532
(52) U.S. Cl. ........................... 426/72; 426/74; 426/575; 426/615; 426/804
(58) Field of Search ................................ 426/575, 615, 426/804, 72, 74

(56) References Cited

U.S. PATENT DOCUMENTS 4,375,481 A * 3/1983 Kuwabara et al. .......... 426/575
4,744,996 A * 5/1988 Rakow et al. .............. 426/575

OTHER PUBLICATIONS

Komatsu et al. Derwent week 197840, Acc–no. 1978–71088A (abstract only of DE 2810453A).*

* cited by examiner

*Primary Examiner*—Helen Pratt
(74) *Attorney, Agent, or Firm*—Joe Nieh

(57) ABSTRACT

A diet food formula for overweight people and diabetics, comprising of agar, carrageenans, alginate, chlorella, spirulina, and water. The diet food formula comprises of all natural materials. The diet food formula cannot be metabolized by the human body after ingestion and will supply the human body with proper nutrients that it requires.

12 Claims, No Drawings

DIET FOOD FORMULA FOR OVERWEIGHT PEOPLE AND DIABETICS

BACKGROUND—Field of Invention

The present invention relates to a diet food formula for overweight people and diabetics.

BACKGROUND—Description of Related Art

People with overweight problems and/or diabetes have extremely limited choices of food that both satisfies their desire to eat and satisfies the body's nutrient requirements.

People with overweight problems are often instructed by their physicians to limit their intake of food while attempting to also maintain a healthy diet by including food with nutrients that the body needs or by taking dietary supplements such as vitamins. However, limiting the intake of food is extremely difficult to do since the body craves for food to fulfill the hunger sensation. Furthermore, the more one tries to limit the intake of food, the more the body craves for them. Therefore attempting to limit food intake to the body often becomes a self-defeating process.

There are numerous variations of diet pills and "diet food" in the market. Most diet pills attempt to limit the body's craving for food, usually they are not very effective. Most "diet food " attempt to provide a low calorie diet, but it is usually in such small quantity that it leaves the body wanting for more food. A diet based on diet pills and "diet food " usually include taking dietary supplements such as vitamins to make up for the deficiency in nutrients due to such a diet.

People with diabetes often face similar limited choice of diet due to their medical condition. Diabetics cannot ingest sugar or starch but still requires the nutrients for their health.

SUMMARY OF THE INVENTION

The present invention is a diet food formula for overweight people and diabetics. The present invention supplies both the volume to satisfy the body's need for food and the nutrients required by the body in one convenient package. The present invention will allow people with overweight problems and diabetes to eat as much as they desire and not worry about eating too much food or not getting sufficient nutrients. The present invention comprises a mixture of agar, carrageenans, alginate, chlorella, spirulina, and water, all of which are natural materials.

DETAILED DESCRIPTION OF THE PREFERRED EMBODIMENT

The preferred embodiment of the present invention comprises of six natural materials: agar, carrageenans, alginate, chlorella, spirulina, and water. Agar is a complex water-soluble polysaccharide and is extracted from red seaweed, such as the Gelidium species and the Gracilaria species. Carrageenans are water-soluble gums and are extracted from certain species of red algae, such as Gigartina, Chondrus, and Eucheuma. Alginate is extracted from brown algae, such as Laminaria and Macricystis, and is also water-soluble. Chlorella and Spirulina have been successfully cultured artificially in many countries. Both Chlorella and Spirulina contain 55% to 65% of protein, which is usable by the human body as a source of protein.

Agar, carrageenans, and alginate are not toxic to human body and can be ingested by humans and animals without any side effects. Furthermore, human body cannot metabolize these materials after ingestion, therefore, there are no caloric intake due to the ingestion of these materials. Fresh water algae, Chlorella, and Spirulina supplies the necessary protein for the human body. This is particularly important for people who are diabetics, who cannot ingest sugar or starch but who still needs the nutrients for their health.

The preferred embodiment of the present invention comprises 0.1 to 30 grams of agar, 0.1 to 30 grams of carrageenans, 0.1 to 45 grams of alginate, 0.1 to 45 grams of chlorella, 0.1 to 45 grams of spirulina, and 100 milliliter of water. The mixture is autoclaved for 20 minutes at 1.5 pounds per square inch pressure on liquid cycle, followed by cooling and packaging for sale.

The present invention may be adapted to different tastes by mixing it with any other ready to eat products, such as special extracts from fresh vegetables and vegetable salad with palm oil. The present invention may also be adapted to different nutritional needs. Nutrients such as vitamins and minerals may be added to the mixture to supply the human body with the necessary nutrients.

What is claimed is:

1. A diet food formula comprising a mixture of:
   agar,
   carrageenans,
   alginate,
   chlorella,
   spirulina,
   whereby the compound is autoclaved in water on liquid cycle.

2. A diet food formula as in claim 1, wherein the mixture is in substantially the proportion of:
   0.1 gram to 30 grams of agar,
   0.1 gram to 30 grams of carrageenans,
   0.1 gram to 45 grams of alginate,
   0.1 gram to 45 grams of chlorella,
   0.1 gram to 45 grams of spirulina,
   whereby the compound is autoclaved in 100 milliliter of water for 20 minutes at 1.5 pounds per square inch pressure on liquid cycle followed by cooling and packaging for sale.

3. A diet food formula as in claim 1, further comprising an artificial food flavor.

4. A diet food formula as in claim 1, further comprising a natural food flavor.

5. A diet food formula as in claim 1, further comprising vitamins.

6. A diet food formula as in claim 1, further comprising minerals.

7. A diet food formula as in claim 1, further comprising dietary food supplements.

8. A diet food formula as in claim 2, further comprising an artificial food flavor.

9. A diet food formula as in claim 2, further comprising a natural food flavor.

10. A diet food formula as in claim 2, further comprising vitamins.

11. A diet food formula as in claim 2, further comprising minerals.

12. A diet food formula as in claim 2, further comprising dietary food supplements.

* * * * *